United States Patent
Paulik et al.

(10) Patent No.: US 6,239,415 B1
(45) Date of Patent: May 29, 2001

(54) PROCESS AND APPARATUS FOR MEASURING ENTHALPY CHANGES BY MEANS OF DIFFERENTIAL THERMAL ANALYZER (DTA) APPARATUS, OPERATING WITH QUASI-ISOTHERMAL HEATING TECHNIQUE

(76) Inventors: Ferenc Paulik, Bogár u. 18/b, H-1022 Budapest (HU); Edit Paulik Bessenyeyné, Apostol u. 11/b, H-1023 Budapest (HU); Krisztina Paulik Walther, Garten Strasse 90, D-95213 Münchberg (DE)

(*) Notice: Subject to any disclaimer, the term of this patent is extended or adjusted under 35 U.S.C. 154(b) by 0 days.

(21) Appl. No.: 09/403,549
(22) PCT Filed: Apr. 24, 1998
(86) PCT No.: PCT/HU98/00041
  § 371 Date: Oct. 25, 1999
  § 102(e) Date: Oct. 25, 1999
(87) PCT Pub. No.: WO98/48265
  PCT Pub. Date: Oct. 29, 1998

(30) Foreign Application Priority Data

Apr. 24, 1997  (HU) .................................................. 9700804

(51) Int. Cl.$^7$ ...................................................... H05B 1/02
(52) U.S. Cl. .......................... 219/497; 219/506; 219/508; 219/494; 374/11; 373/136
(58) Field of Search ..................................... 219/497, 499, 219/501, 505, 494, 507, 508, 490–492; 374/10, 11, 101–103, 1; 307/1 A; 373/135, 136

(56) References Cited

U.S. PATENT DOCUMENTS 4,812,051  3/1989  Paulik et al. .
4,821,303  4/1989  Fawcett et al. .
5,842,788  * 12/1998  Danley et al. .......................... 374/10
6,095,679  * 8/2000  Hammiche et al. ................... 374/11

OTHER PUBLICATIONS

Bityutskaya et al, "An Automated Quantitative DTA Research System", Industrial Laboratory, vol. 56, No. 4 Apr. 1990, pp. 445–447.

Amengual et al, "An experimental set–up for thermal analysis and DSC: its application to the hysteresis cycles in shape memory alloys", Journal of Physics E: Scientific Instruments, vol. 22, No. 7, Jul. 1989, pp. 433–437.

Zynger, "Automated, Stepping Differential Calorimeter for the Analysis of Purity", Analytical Chemistry, vol. 47, No. 8, Jul. 1975, pp. 1380–1384.

Anjard, Sr. "The Microelectronics Applications of Differential Scanning Calorimetry for Packaging and Materials–Including Solder Pastes", Microelectronics and Reliability, vol. 25, No. 1, 1985, pp. 9–16.

* cited by examiner

Primary Examiner—Mark Paschall
(74) Attorney, Agent, or Firm—Venable; Gabor J. Kelemen (57) ABSTRACT

In a thermal analysis process for investigating thermal phase transformations, a sample and a reference substance are placed into a furnace with rising temperature of a predetermined rate operated by a programmed temperature controller. The temperatures of the sample and reference substance are sensed by temperature sensors. The temperature difference is determined by a device having an output signal which is proportional to the temperature difference and which is generated by the known quasi-static heating technique. The temperature difference is automatically controlled continuously so that the thermal phase transformation of the sample takes place at a constant rate. The output signal which is function of time t, is integrated with respect to time by an integrating unit and the output signal of the integrating unit is further transformed into a signal dependent on the temperature of the sample.

5 Claims, 8 Drawing Sheets

PROCESS AND APPARATUS FOR MEASURING ENTHALPY CHANGES BY MEANS OF DIFFERENTIAL THERMAL ANALYZER (DTA) APPARATUS, OPERATING WITH QUASI-ISOTHERMAL HEATING TECHNIQUE

FIELD OF THE INVENTION

The invention relates to a process and apparatus capable of measuring the enthalpy change or eventually its change rate as a function of the temperature of a sample by means of a DTA apparatus operating with quasi-isothermal heating technique.

PRIOR ART

Physical and chemical transformations taking place on heating of materials always involve variation of the enthalpy, the consequence being that the temperature of sample changes differently from that of its environment. For almost a century, the study of these processes has been carried out by means of differential thermal analysers, i.e. by DTA instruments during heating or cooling. However, by using these equipments, in the majority of cases, only a deteriorated picture of processes taking place can be obtained either at heating or cooling of the samples. The reason for this is that the course of curves is significantly influenced by the experimental conditions, such as the rate of heating or cooling, the rate of heat transfer between the sample and its environment, the magnitude of the transformation heat, etc. Thus, according to experience, phase diagrams of unknown structures for multi-component systems are very difficult to be constructed by a traditional DTA apparatus.

This problem can very well be studied in the opposite way, when we compare the results of traditional DTA studies with a well-known phase diagram. In this case, namely, we have a basis for comparison, we know, how and at which temperature the processes studied would have taken place under ideal conditions.

Figure 1A:
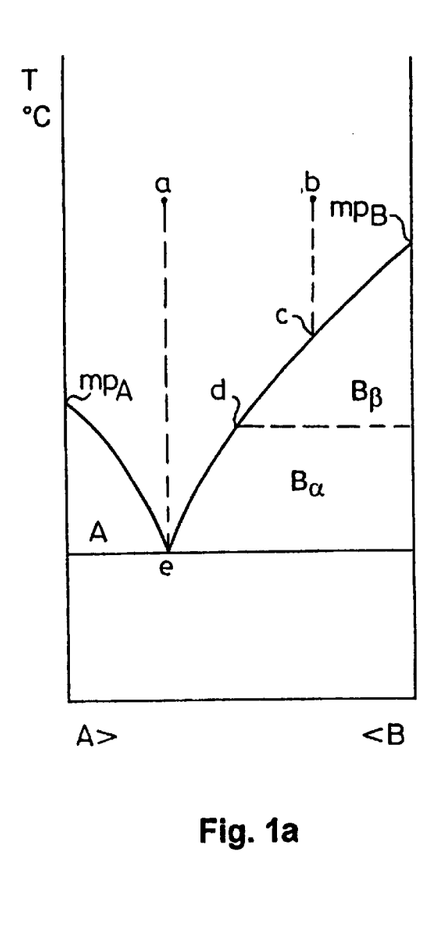
FIG. 1a shows the phase diagram of the eutectic mixture of components A and B.
Figure 1B:
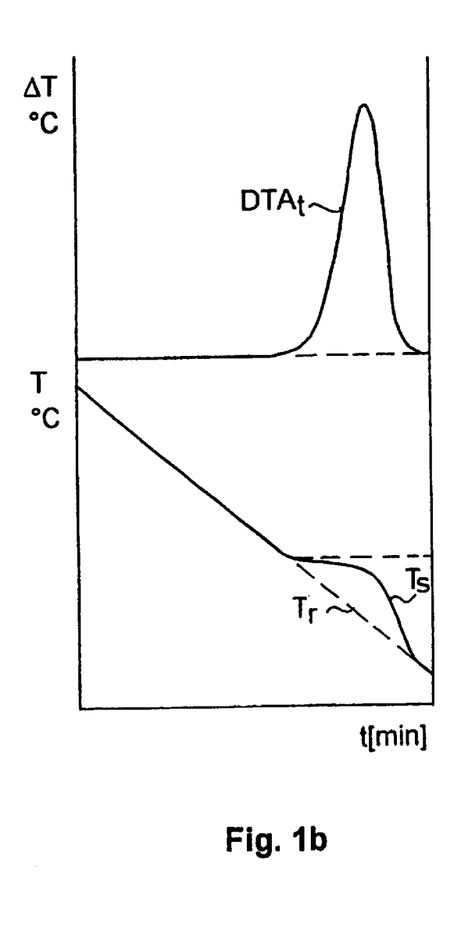
FIG. 1b represents the DTA$_t$ curve of a non complex process, e.g. the a-e phase transformation of this mixture, changes in the sample temperature, T$_s$, and in that of the reference material, T$_r$, as functions of time.
Figure 1C:
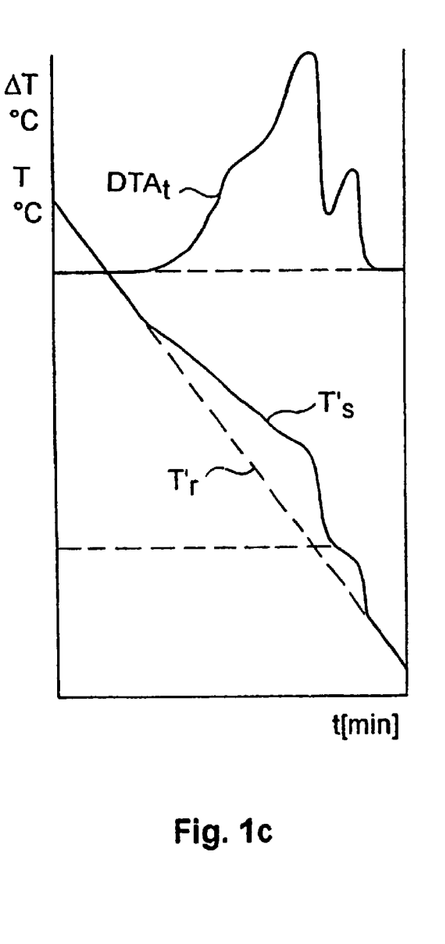
FIG. 1c shows the DTA$_t$ curve of a complex, partly non-isothermal d-c-d-e transformation, together with the traditional T$_s$ and T$_r$ curves.

Such a phase diagram is shown in FIG. 1a. FIGS. 1b and 1c show the results of DTA studies on two samples with different compositions. Phase diagram 1a represents the equilibrium for a eutectic mixture of components A and B in a coordinate system the ordinate of which is temperature, and the abscissa is composition.

Symbols in FIGS. 1b and 1c have the flowing meanings:

$DTA_r$=traditional DTA curve as a function of time $T_s$=temperature change in the sample as a function of time $T_r$=temperature change in the inert material as a function of time $\Delta T$ change=in the temperature difference $T_s-T_r$ proportional to enthalpy variation The ordinates for these curves are temperature and temperature difference.

If we study the system at cooling by starting from point a, it can be established from FIG. 1a that at reaching the eutectic temperature e, the eutectic mixture begins to precipitate from the melt and the system solidifies fully without any change in the temperature.

At studying the system by the known DTA apparatus, as is shown in FIG. 1b, however, it turns out that this phase transformation has not taken place in an isothennal way, but in a wide temperature range, during quite a long time-period. It is clear from FIG. 1b, namely, that the temperature $T_s$, turns back to the temperature $T_r$ of the reference material, only with a delay. It is obvious that in the opposite case, when the goal is to construct a phase diagram, this phenomenon is very misleading.

Starting from point b of FIG. 1a we can see the following: at reaching the temperature measured in point c, modification $B_\beta$ starts to precipitate, which process continues up to point d, in a non-isothermal way. At this temperature, modification $B_\beta$ already precipitated transforms in isothermal way into modification $B_\alpha$, and later only this modification precipitates from the melt, also in a nonisothermal way. At last, at eutectic temperature e, the system solidifies isothermally.

The results of the study performed by the DTA apparatus shown in FIG. 1c are almost impracticable, because, in this case, of the more elementary processes taking place with a strong delay and overlapping. Isothermal and non-isothermal processes cannot be differentiated and identified on the $DTA_r$ and $T_s$ curves. Consequently, in the opposite case, no phase diagram could be constructed from these curves.

We have chosen these two examples, since they can be generalized for the whole area of thermal analysis. Phase transformations like that shown in FIG. 1b are characteristic for individual, isothermally occurring thermal transformations, such as certain decomposition reactions, modification and state changes, etc., while that shown in FIG. 1c is characteristic for complex, non-isothermal types of transformations, like e.g. the big family of solid state reactions.

Thus we have seen that in the traditional way, the course and characteristic temperatures of both transformation types can be determined only inaccurately, or not at all.

To the contrary, the apparatus operating according to the principle patented by J. Paulik, F. Paulik and M. Arnold under the number U.S. Pat. No. 3,344,654, the study of the first type of transformations can be performed by a large accuracy. This is illustrated in FIGS. 3b and 4b. However, the second type of transformations cannot be investigated satisfactorily either by the use of this known procedure.

This invention relates to a process and apparatus elaborated by a further development of the method applied in the previously mentioned patent, the use of which makes the determination of the enthalpy changes in the second type of complex and non-isothermal transformations also possible.

For the elimination of similar mistakes originating from the conditions of the experiment in the thermal gravimetric measuring technique, J. Paulik, F. Paulik and L Erdey elaborated the first static thermal analytical method, the so-called quasi-isothermal thermogravimetric procedure, characterised thereby that the heating of the furnace is controlled by the rate of the weight change. This method is described in the U.S. Pat. No. 3,344,654. This is a well-established method applied successfully already for decades. Later on, Rouquerol also elaborated a similar procedure, in which heating was controlled by the rate of gas evolution occurring during decomposition.

However, the above methods cannot eliminate the problems caused by the experimental conditions in DTA and DSC, i.e. differential scanning calorimetric measurements. The previously mentioned patent, U.S. Pat. No. 4,812,051 has been elaborated by J. Paulik, F. Paulik and M. Arnold for performing such measurements, i.e. the methods of quasi-isothermal differential thermal analysis, Q-DTA, and quasi-isothermal differential scanning calorimetry, Q-DSC.

Figure 2:
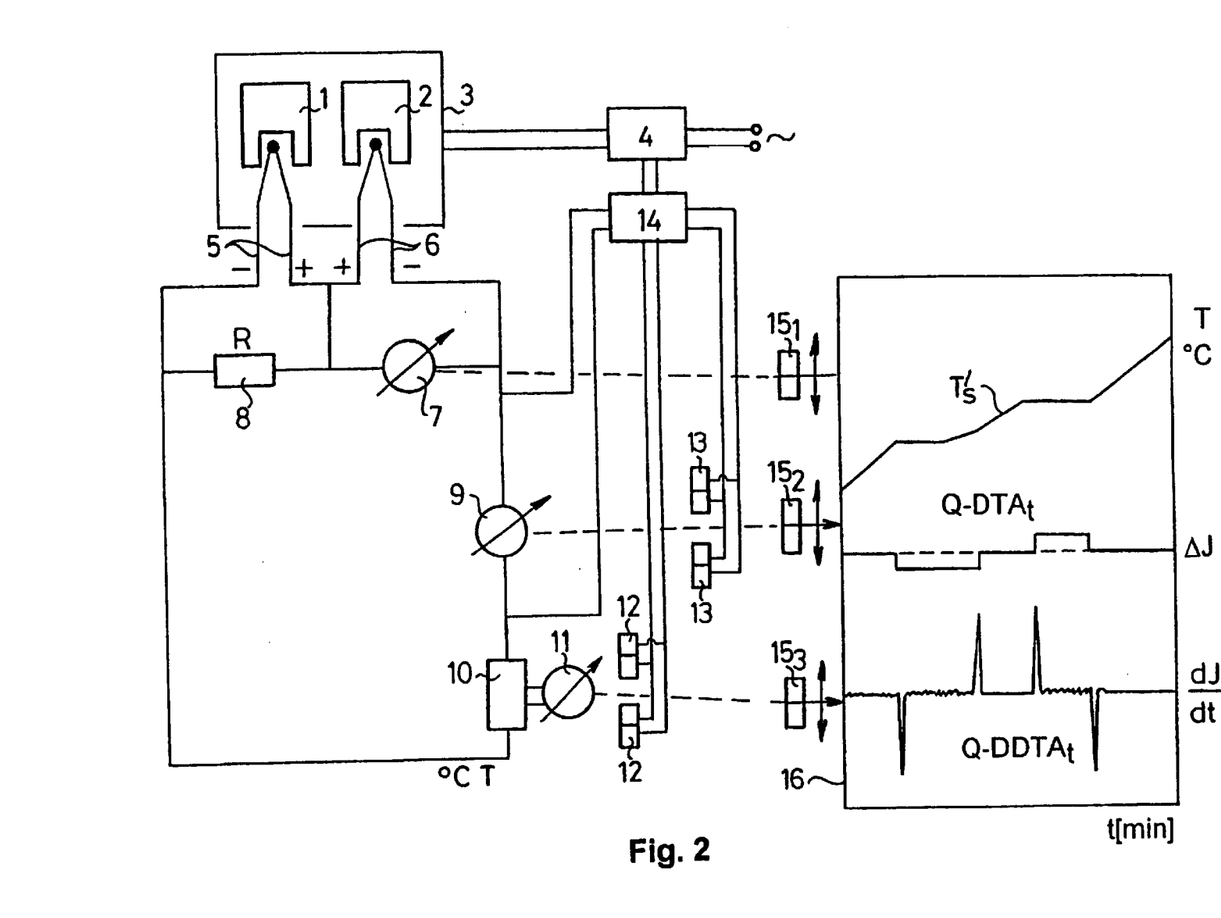
FIG. 2 illustrates an example for the embodiment of the known quasi-isothermal Q-DTA apparatus.

In FIG. 2, a scheme of the most important elements of the quasi-static temperature controlling system described in patent U.S. Pat. No. 4,812,051 is shown. We present this, in order to make the recognition of the invention more unambiguous. It is seen that reference material 1 and sample 2 are placed into furnace 3 in separate containers, to which furnace 3 programmed temperature controller 4 is connected. The temperatures of both, reference material 1 and sample 2, are sensed by temperature sensors 5 and 6, which are thermocouples. By temperature measuring device 7 is the temperature of sample 2 measured. This temperature measuring device 7 is, in the present example, a galvanometer, the output signal of which is recorded by writer $15_2$ on paper 16. A so-called symmetrising resistance 8 is connected parallel to temperature sensor 5. At the non-common point of symmetrising resistance 8 and temperature sensor 7, differentiating unit 10 and temperature difference measuring device 9 are connected in series. The latter measures the difference in the thermal potentials of oppositely coupled thermocouples 5 and 6, i.e. the difference between the temperatures of reference material 1 and sample 2. The output of temperature sensor 7 measuring the temperature of sample 2 is connected via galvanometer 11 to writer $15_3$. The recorder is equipped with three $15_1$; $15_2$; $15_3$ writers, and the paper 16. Similarly, temperature difference measuring device 9 is also connected to recording paper 16 through another writer, $15_2$. The output of differentiating member 10 is coupled to writer $15_3$ via derived signal sensor 11, which, in the present embodiment, is also a galvanometer, which, in turn, is connected again to recording paper 16. Recording paper 16, thus shows how temperature $T'_s$, i.e. sample temperature, changes as a function of time during quasi-static temperature control. The Q-DTA$_t$ signal is visible as well, which illustrates the temperature difference between reference material 1 and sample 2, i.e. the change of a signal proportional to the enthalpy change, ΔJ, accompanying the transformation, in joule. In addition, curve Q-DDTA$_t$ is shown, which symbolises the rate of enthalpy variation, dJ/dL.

Temperature control occurs so that to both, temperature difference measuring device 9 and differentiating member 10 are provided with two limit switches 12 and 13, the outputs of said limit switches 12 and 13 are coupled to switching unit 14, which, in turn, controls also programmed temperature control unit 4.

This apparatus operates so that programmed temperature control unit 4 increases the temperature of furnace 3 traditionally—i.e. by the predetermined uniform rate—till in sample 2 some physical or chemical transformation starts. At this point, the multifunctional part of the apparatus consisting of elements 10,11,12,14 and $15_3$ becomes operative. This part serves several purposes. It senses by an increased sensitivity, the start of transformation, eliminates a shift in the base line of the DTA signal before transformation, and adjusts the heating control from the traditional, non-isothermal mode to the quasi-isothermal mode of operation. The signal of the thermal potential difference of oppositely coupled temperature sensors 5 and 6 is derived by differentiating unit 10, while galvanometer, which is the derived signal sensor 11 measures the change in the derived signal. The rapidly increased signal of starting transformation is sensed by limit switches 12, and they send a signal to multifunctional switching unit 14. At that, this latter gives a countervoltage onto the poles of the temperature difference measuring device 9 by means of an electronic device, for compensating its deflection and bringing it back to zero. After that, control switching unit 14 switches to quasi-isothermal operating mode, i.e. after that, the heating of the furnace is controlled by the potential difference of oppositely coupled temperature sensors 5 and 6 by means of galvanometer 9 and limit sensing switches 13.

In fact, limit switches 13 provide the limit value concerning the rate of transformation and enthalpy variation. Switching unit 14, namely, is also in an operation connection to these limit switches 12 and 13. At the decrease of temperature, the rate of transformation decreases as well. As a consequence, signal $Q_{DTAt}$ changes, thus heating starts again. Such an intervention lasts only for seconds, but it is repeated periodically until transformation is complete.

Summarisingly, the above programmed temperature control system enables a temperature difference between sample 2 and furnace 3 so that transformation can take place only with a very small but strictly constant rate, by orders of magnitude smaller Fan in the traditional method described in the introductory part Thus, the predetermined rate of the transformation is controlled by transformation itself, through a very fine variation of temperature on the basis of feed-back U.S. Pat. No. 4,812,051 describes differential scanning calorimeters (DSC) as well, which may also be used instead of a DTA apparatus for quantitatively determining the changes of entalphy caused by transformations.

Figure 3A:
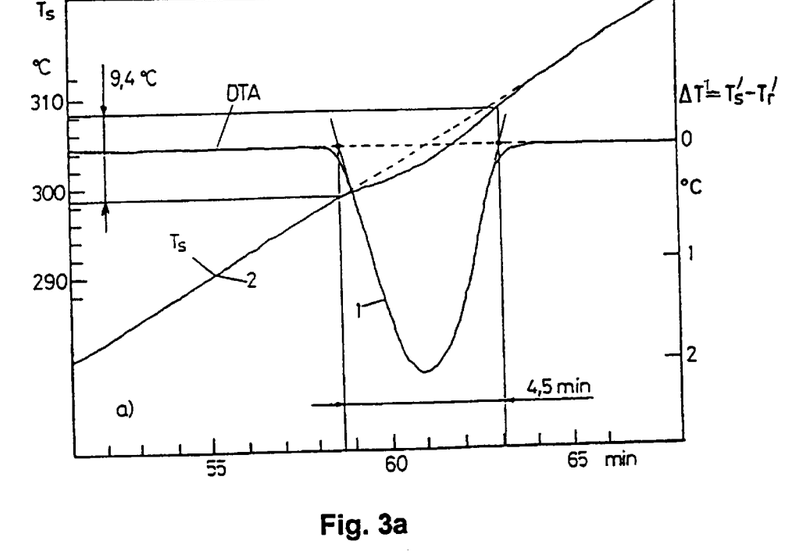
FIGS. 3a and 3b show the DTA and T$_s$, and Q-DTA$_t$ and T$_s$ curves for the modification change of potassium perchlorate taken by the known, traditional method, FIG. 4a, similarly to FIG. 1a, represents the phase diagram of the eutectic mixture of components A and B.
Figure 3B:
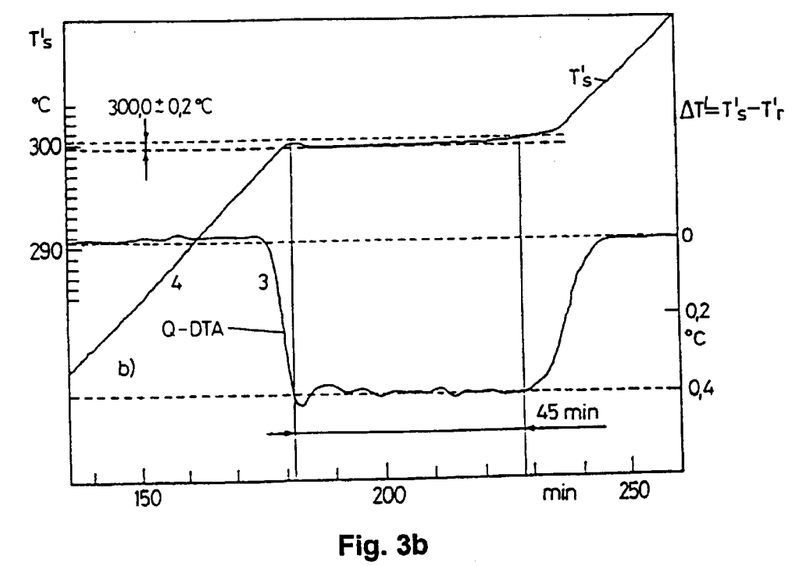
Figure 4A:
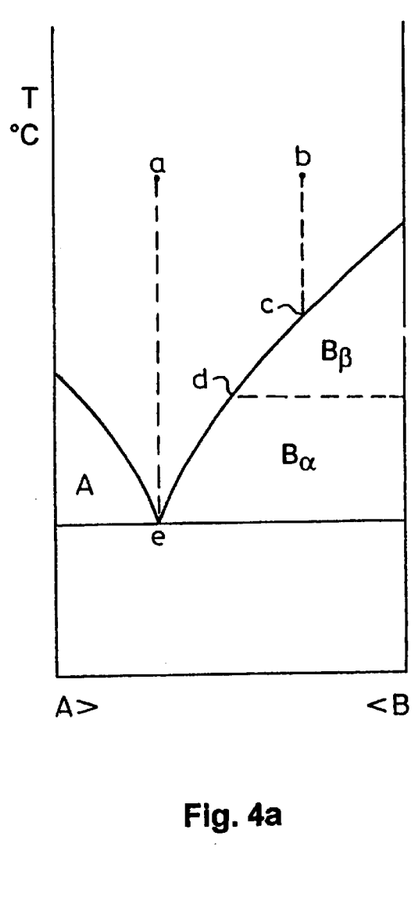
Figure 4B:
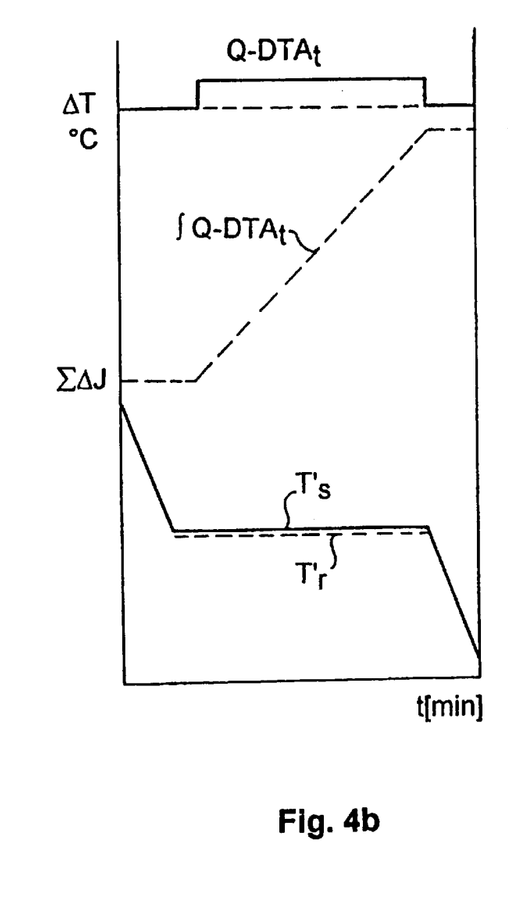
FIG. 4b shows the results of the Q-DTA study of the well known sample from FIG. 1b, with a non-complex, isothermal transformation, FIG. 4c, similarly again to FIG. 1c, shows the results of the Q-DTA study characteristic for complex, partly non-isothermal processes, taken by the apparatus according to patent number U.S. Pat. No. 3,344,654.

This measuring technique eliminates the deteriorating effect of experimental conditions on the course of formations, consequently, by its mean, at least the course of not complex and isothermal phase transformation processes can be followed realistically, and transformation temperatures can be determined with a high accuracy. This is illustrated on the example of the modification change of potassium perchlorate at 300° C. in FIG. 3. Symbols mean the following:

Q-DTA$_t$=modified form of the DTA curve illustrating the rate of transformation as a function of time T'$_s$=modified form of the temperature change in the sample as a function of time ΔT'$_r$=modified form of the temperature change in the reference material as a function of time ΔJ=enthalpy variation expressed in joule ΔJ$_1$, ΔJ$_2$, . . . =partial enthalpy variations exrpessed in joule ΣΔJ=total enthalpy variation expressed in joule dJ/dt=rate of the enthalpy variation expressed in joule FIG. 3a shows the curves for modification change in potassium perchlorate taken by the traditional DTA technique, i.e. by the non-isothermal heating technique, whereas those obtained by the quasi-isothermal technique, i.e. by Q-DTA, are shown in FIG. 3b. The course of DTA and T$_s$ curves in FIG. 3a illustrates that under the given conditions, modification change takes place in the temperature interval of 299–308° C., in a non-isothermal way.

To the contrary, the course of curves in FIG. 3b proves that under quasi-isothermal conditions, the modification change in the sample occurred isothermally, at 300±0.2° C., which temperature of the modification change could be determined in this case with a high accuracy.

Thus, with this type of transformations we obtain unambiguous answers to all of our arising questions. The situation is different for the other type of transformations, for those of a partly or fully non-isothermal, complex nature. The Q-DTA measuring process described above eliminates the deteriorating effects of experimental conditions also in the case of such processes, but the interpretation of Q-DTA$_t$ and T'$_s$, curves remains uncertain. This can be judged from the course of curves in FIGS. 4b and 4c, on comparing them to curves in FIGS. 1b and 1c. Curves 1b and 4b, as well as 1c and 4c are taken on samples of the same composition, the only difference being that curves in FIGS. 1b and 1c are taken by the traditional DTA method, whereas curves in FIGS. 4b and 4c by the quasi-isothermal method described above. The basic idea for this invention has been provided by a deep analysis of curves in FIGS. 4.

Figure 4C:
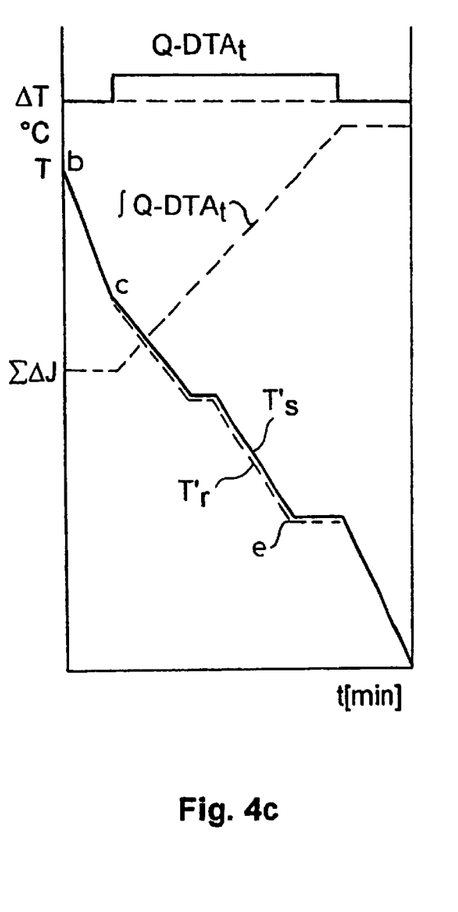

It is clearly seen in FIGS. 4b and 4c that curve Q-DTA$_t$ provide information only about the fact that the rate of enthalpy variation was, in fact, small and constant. Thus its recording is needed for checking the heating control, but in order to make this better interpretable, this signal should be transformed further. In the case of complex processes—as it is seen in FIG. 4c—signal T'$_s$ is the only carrier of information. However, this signal in itself is, in the majority of cases, difficult to interpret The reason for this is that this curve carries two kinds of information simultaneously. For one, it indicates a big change in the temperature of the furnace, for second, it provides information about a small temperature change caused by the enthalpy variation of sample 2. These two kinds of information, however, melt together in curves T'$_s$ and are difficult to distinguish.

SUMMARY OF THE INVENTION

If we integrate curve Q-DTA$_t$ indicating the enthalpy variation in an appropriate way, we obtain curve ∫Q-DTA$_t$ shown in FIGS. 4b and 4c. This curve informs still only about the measure of the enthalpy change, from its linear course we cannot draw any conclusion concerning the transformation. However, the result of the study becomes dear and interpretable, if curve ∫Q-DTA$_t$ is drawn, according to the invention, by an electronic device operating similarly as the X-Y writer, as a function of sample temperature T'$_s$, as it is seen in FIG. 6c.

The invention relates to a temperature controlling process for investigation of thermal phase transformations, wherein a sample and a reference substance are placed into a furnace with rising temperature of a predetermined rate operated by a programmed temperature controller, the temperatures of sample and reference substance are sensed by temperature sensors, the difference between the temperatures T'$_s$, T'$_r$ of the sample and reference substance is determined by a temperature difference measuring device the output signal being Q-DTA$_t$, which, in turn, is coupled to an element forming a signal proportional to the temperature difference, and when a difference between the temperature of the sample T'$_s$ and that of the reference substance T'$_r$ is generated, these are measured by the known quasi-static heating technique, and a difference is kept between them automatically and controlled by the transformation itself continuously at such a value that the transformation should take place at a constant rate orders of magnitude smaller than in the other known solutions.

The essence of the process lies in integration of signal Q-DTA$_t$ obtained as a function of time and proportional to the difference in the temperatures of the sample T'$_s$ and reference substance T'$_r$, then transforming the signal ∫Q-DTA$_t$ obtained at the output of integrating unit as a function of time into a signal depending on the temperature of the sample, ∫Q-DTA$_T$, preferably a further differentiation of integrated signal ∫Q-DTA$_T$ in order to obtain signal d∫Q-DTA$_T$.

The invention relates further to a temperature control system for investigation of thermal phase transformations using DTA device known per se, wherein sample and reference substance are placed into a furnace with rising temperature of a predetermined rate, the furnace is connected to a programmed temperature controller, both the sample and reference substance are coupled to temperature sensors, these temperature sensors are coupled oppositely, and a temperature sensor measuring the sample temperature T$_s$, is coupled to their free contacts in series, a symmetrising resistor, further on, to the free contacts of the oppositely coupled temperature sensors a differentiating unit and a temperature difference measuring device sensing the difference between sample and reference substance are connected in series, the output of which is connected via the integrating unit onto a display means and a recorder, and the output of the differentiating member is also connected to a device signal sensor and the recorder, the deflection of the device signal sensor is sensed by limit switches the output contacts of which are connected to the input of the programmed temperature controller via a multifunction switching unit, and, similarly, the output contact of the temperature difference measuring unit is also coupled to switching unit.

The essence of the system lies in connection of an integrating unit to the output of the temperature difference measuring unit the output of which integrating unit is connected to a signal converter, the further two inputs of which are coupled to the temperature measuring device measuring the sample temperature for the generation of transformed signal ΔtΔ(T$_s$) at the output of the signal converter, whereas to the output of signal converter a display for the transformed signal is connected the output of which is coupled to a recorder.

The subject of the invention is a temperature control system for investigation thermal transformation using the DSC-device known per se, wherein sample and reference substance are placed in furnace having double heating system, one heating element of which is controlled by programmed temperature controller the inputs of which are connected to a temperature difference measuring unit the inputs of which are connected to temperature sensors, the first output of device is connected to limit switch coupled to the second heating elements and to a differentiating unit, the second output of said device is connected to the recorder.

The essence of the temperature controlling system lies in that the connection of an integrating unit to the output of the temperature difference measuring device the output of which integrating unit is connected to a signal converter, whereas to the output of the signal converter a display for the transformed signal is connected the output of which is coupled to a recorder.

Preferably the connection of a differentiating unit to the output of the signal converter, the output of which is also connected to a display, the signal of which is lead to recorder.

BRIEF DESCRIPTION OF THE DRAWINGS

FIG. 7a is the phase diagram of the eutectic mixture of components A and B, as in FIG. 1a, FIG. 7b corresponds to FIGS. 1b and 4b, the difference being that it is taken by the apparatus of this invention, FIG. 7c corresponds to FIGS. 1c and 4c, the difference being that it is taken by the apparatus of this invention.

DESCRIPTION OF THE PREFERRED EMBODIMENTS

Figure 5:
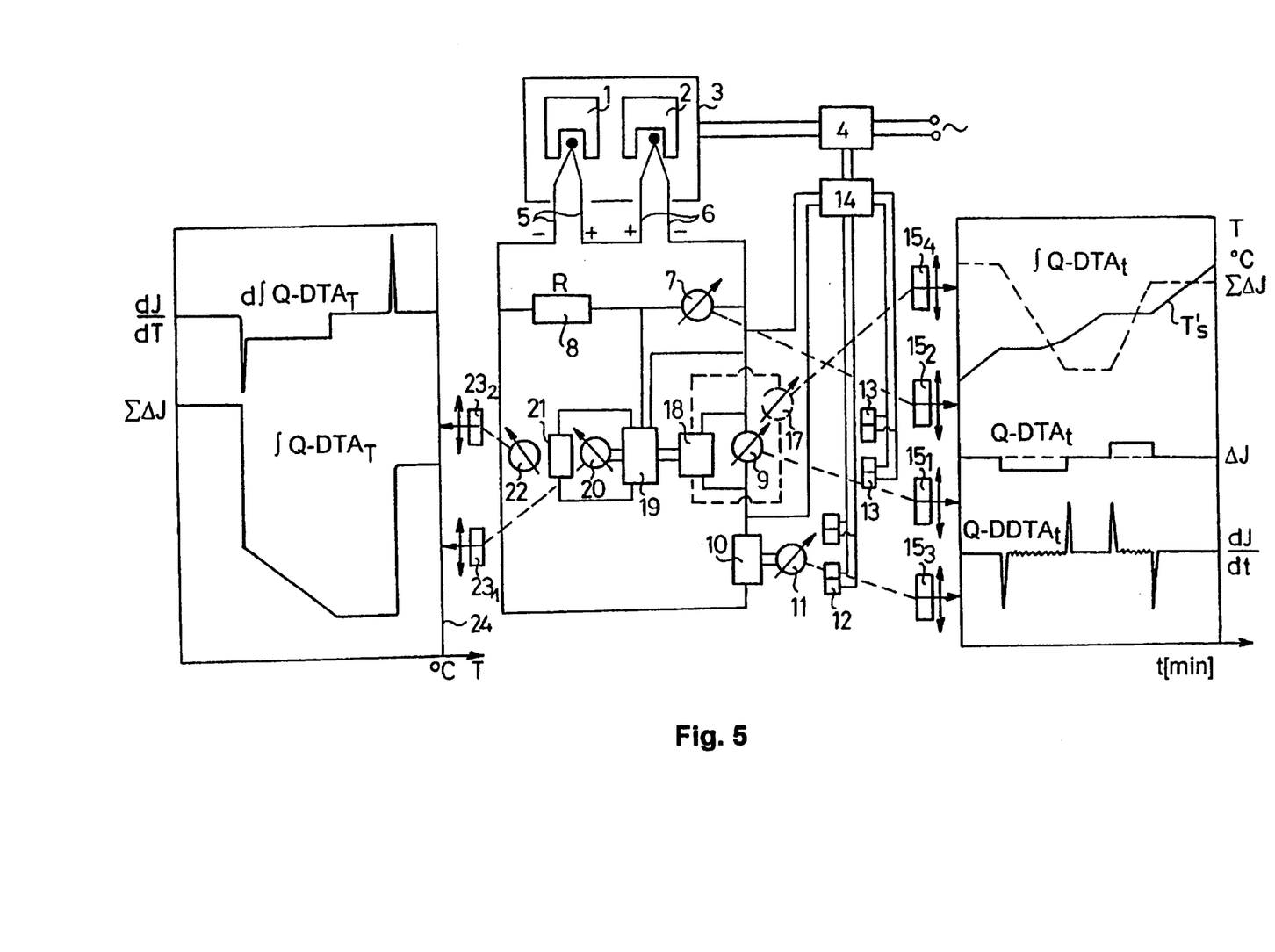
FIG. 5 shows an embodiment of the present invention, the quasi-isothermal apparatus.

Thus, the solutions known up to now are represented in FIGS. 1–4, now, we turn to FIG. 5 showing an embodiment of the apparatus of the present invention. The elements not described here are the same as shown in FIG. 2. What is shown there, is furnace 3, containing a reference material, 1, and the sample 2, where to reference material 1 a temperature sensor 5, and to sample 2 a temperature sensor 6 is connected. Temperature sensors 5 and 6 are, in this example, thermocouples. One of the free outputs of the two oppositely coupled temperature sensors 5 and 6 is connected to temperature measuring device 7 measuring the sample temperature $T_s$, which is, in this example, a galvanometer, coupled to the other output of temperature sensor 5 via a symmetrising resistance 8. Temperature difference measuring device 9 is connected to the not common points of temperature sensors 5 and 6, which generates a signal proportional to the temperature difference between reference material 1 and sample 2. This is also a galvanometer, which then is connected to recording paper 16 of a recording apparatus through writer $15_2$. Temperature measuring device 7 records the temperature change of the sample 2 by means of writer $15_1$ on recording paper 16. To the free, not connected points of temperature sensors 5 and 6, differentiating unit 10 and temperature difference measuring device 9 are coupled in series. Differentiating unit 10 is connected to writer $15_1$, through derived signal measuring unit 11. The writers $15_1$; $15_2$; $15_3$ record the signal on paper 16 depending on requirements. An integrating unit, 18, is coupled parallel to temperature difference measuring unit 9, the two outputs of which are connected through the light signal of a galvanometer to writer $15_4$, which then records the output signal of integrating unit 18 on paper 16.

The symbols in FIG. 5 are the following:

∫Q-DTA$_t$=integrated form of function Q-DTA$_t$ as a function of time

∫Q-DTA$_T$=integrated form of function Q-DTA$_T$ as a function of sample temperature (output signal of signal converter 19)

d∫Q-DTA$_T$=derived form of function ∫Q-DTA$_T$ as a function of sample temperature dJ/dt=rate of enthalpy change in joule as a function of time dJ/dT=rate of enthalpy change in joule as a function of sample temperature T Thus, it is well seen in FIG. 5 that four signals are recorded on paper 16. One of them shows the time course of sample temperature $T_s$, which is a signal proportional to the output of temperature measuring device 7. The second one is the Q-DTA$_t$ signal proportional to enthalpy change ΔJ which is coupled to the output of the temperature difference measuring unit 9. The next one is the dJ/dt signal, proportional to the output signal of the differentiating unit 10 of the bridge represented as a function of time. Finally, signal ∫Q-DTA$_t$ is also shown, that is proportional to the signal appearing at the output of integrating unit 18 being the total variation in the enthalpy,i.e. ΣΔJ.

The output of integrating unit 18 is connected to a signal converter, 19, the two inputs of which are coupled to the output of device 7 measuring the temperature of the sample 2. Thus, the two inputs of signal converter 19 receive a signal proportional to the temperature of sample, $T_s$, its further two inputs the signal of the output signal of integrating unit 18, i.e. it generates essentially the integrated signal of the output of temperature difference measuring device 9 as a function of sample temperature $T_s$. At the output of converter 19, ΔT(t) appears transformed to ΔT($T_s$). The output of integrating unit 18 is lead to differentiating unit 21, and the outputs of both integrating unit 18 and differentiating unit 21 are connected to sensors 20 and 22, which may also be galvanometers, and finally to writers $23_1$ and $23_2$ which record curves ∫Q-DTA$_T$ and d∫Q-DTA$_T$ on recording paper 24.

Figure 7A:
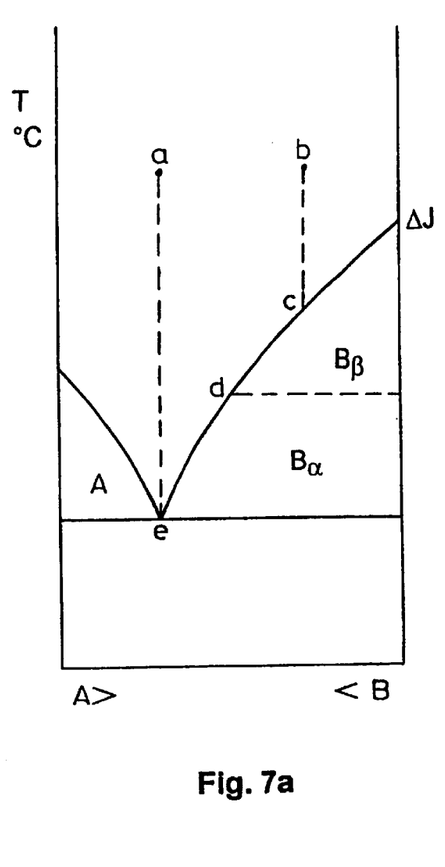
Figure 7B:
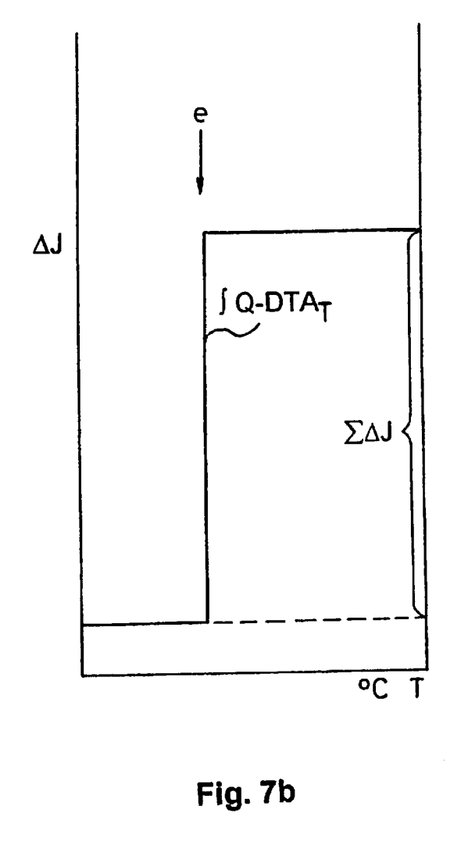

It can be well seen on the curves that ∫Q-DTA$_t$ carries only quantitative information concerning the elementary processes. As to the detailed course of transformations, sample temperature curve $T_s$ is the information carrier. At the left side of FIG. 5, ∫Q-DTA$_T$ is shown, which, however, represents the individual values already as functions of sample temperature, $T_s$. In certain cases this curve is difficult to interpret, as is shown in FIG. 7b, thus it seems to be expedient to differentiate it again. The resolution of the d∫Q-DTA$_T$ signal thus obtained is significantly higher.

$T_s$ and Q-DTA curves of the invention should be transformed corresponding to the type of phase transformation to be studied.

Figure 6:
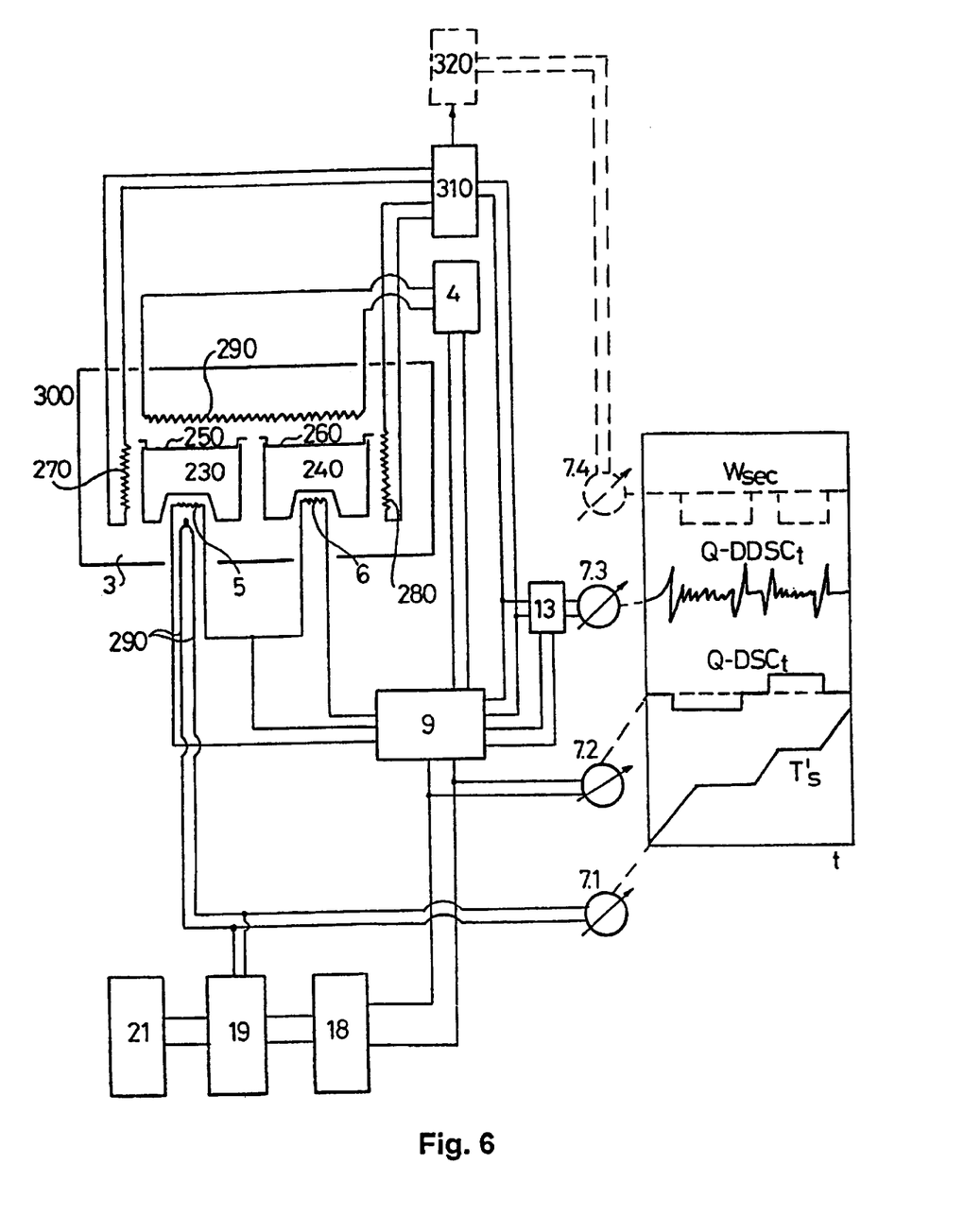
FIG. 6 shows a temperature measuring and registrating system in which a DSC is used.

FIG. 6 shows a preferred embodiment using DSC. A DSC differs from a DTA only in that the sample container 250 of the reference substance is empty in case of traditional measurements and the temperature of the sample container 250 is measured instead of that of the sample 230. The DSC measures also the specific heat variation of the sample 230 besides the entalphy variation of the transformation. If a reference substance 240 of heat capacity nearly identical with that of the sample 230 is nevertheless placed in the sample container, the DSC can be used to plot a regular DTA curve. The two systems differ from other also in that the DSC has a double heating system. The double heating system has three heating elements 270, 280 and 290. The heating element 290 is connected to the programmed temperature controller 4, heating elements 270 and 280 are connected to limit switch 310. The temperature sensors 5 and 6 are connected to multifunction temperature difference measuring device 9 producing a signal proportional to the temperature difference. The temperature of the sample 230 is measured by a thermocouple 290 the output of which is connected to a galvanometer 7.1 and to signal converter 19. The outputs of the device 9 are connected to the input of the integrating unit 18, the output of which is connected to signal converter 19, the output of which is then connected to differentiating unit 21. The same outputs of device 9 are connected to galvanometer 7.2. Further outputs of device 9 are connected through differentiating unit 130 to galvanometer 7.3 and to a further input of differentiating unit 130, which is connected to limit switch 310, as well. The limit switch 310 has an output connected through an electricity meter 320, measuring the consumption of heating elements 280 and 270. The measured data enables to compare the curve Q-DSC$_t$ with the consumption using for registration a galvanometer 7.4.

The measuring technique of this invention makes the investigation of the following types of processes possible:

Type 1

Figure 7C:
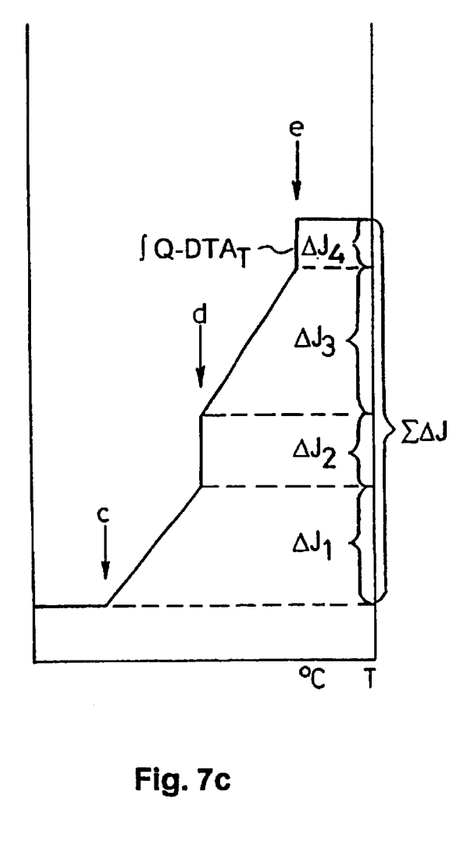

This group contains the melting or solidification of pure compounds shown in FIG. 3b, modification changes illustrated as processes d in FIGS. 4c and 7c or the melting and solidification of eutectic mixtures of multicomponent systems marked in FIGS. 4b, 4c, 7b and 7c by an arrow signed by e. These processes are reversible, lead to equilibrium and under ideal conditions, they are isothermal. Temperature curve T$_s$ and curves Q-DTA$_t$ can be interpreted well without any transformation, as is seen in FIG. 3b.

Type 2

To this type belong complex, non-isothermal transformations of multicomponent systems, in their case the application of quasi-isothermal measuring technique is indispensable, as slow diffusion plays here a key role in spite of the fact that these processes are also reversible and lead to equilibrium. It is easy to acknowledge that due to the deteriorating effect of diffusion it is not indifferent whether we allow these processes to take place at a rate 2–3 orders of magnitude slower than the traditional one.

In this case, it is usually necessary to transform T$_s$ and Q-DTA$_t$ curves according to this invention, especially if non-isothermal sections are wedged between elementary processes. According to our experience, on the basis of curves $\int$Q-DTA$_T$ thus transformed the characteristic temperatures of elementary processes can be determined by a high accuracy—as it is seen in FIG. 7c as well—, that is very important for the construction or checking of phase diagrams for multicomponent systems.

Type 3

The procedure according to this invention is especially important in these types of transformations, which are mainly reactions taking place between solid phase components, the so-called solid phase reactions. These transformations, namely, except for several exceptions, do not take place with weight change or gas evolution, thus they cannot be investigated by the methods of thermogravimetric, TG, TGG or thermal gas analytical, EGA, methods. For studying them, only the DTA method based on measuring enthalpy changes, or DSC methods are available, though solid phase reactions are very often used e.g. in silicate chemistry or in construction and ceramic industry, etc.

Figure 8A:
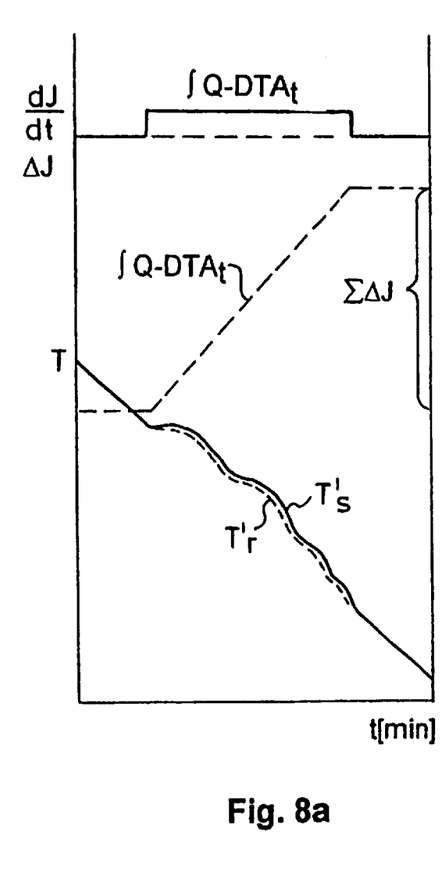
FIG. 8a shows the curve representing the course of a complex transformation consisting of more overlapping, non-isothermal processes, taken by the traditional DTA apparatus.
Figure 8B:
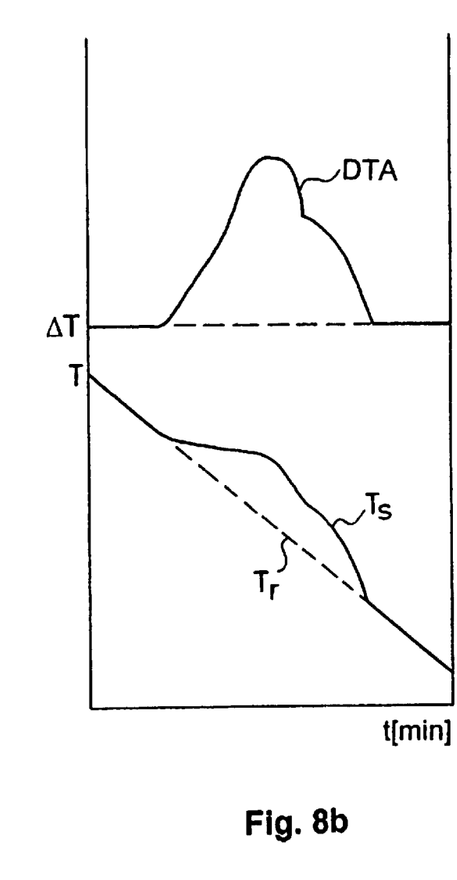
FIG. 8b shows the curves of the same transformation taken by the apparatus in patent U.S. Pat. No. 3,344,654.
Figure 8C:
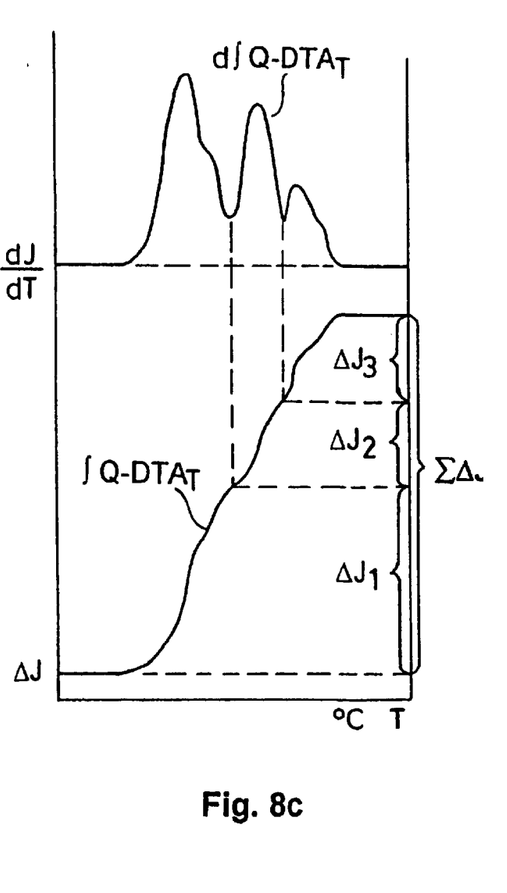
FIG. 8c shows the curves of the same transformation as taken by the apparatus of the present invention.

These reactions occur spontaneously with heat evolution. They do not lead to equilibrium. They are usually very complex processes, consisting of several elementary reactions, e.g. the reaction of CaO and $SiO_2$, taking place at different rates and partly or totally overlapping each other. Diffusion plays also here a very important role. Due to all this, the resultant course of the reaction is totally irregular and from case to case different Experience shows that in such cases the differentiation of curve $\int$Q-DTA$_T$ described in this invention, i.e. the generation of curve d$\int$Q/DTA$_T$ is indispensable, as it is shown in FIG. 8c.

Type 4

For transformations belonging into this group there is abundant experience. These are the decomposition of pure compounds under quasi-isothermal, quasi-isobar conditions, which can be well studied by the methods of thermogravimetry and thermal gas analysis, as well. In these cases, the invention makes rather the determination of the enthalpy changes accompanying the elementary processes possible.

Determination of the Enthalpy Variation

Curves $\int$QDTA$_T$ assist not only the interpretation of transformations, but they also enable us to determine the partial enthalpy changes accompanying the elementary processes of a transformation, i.e. $\Delta J_1$, $\Delta J_2$, etc. even by a much higher accuracy than till now. The total entalpy variation, $\Sigma \Delta J$ can be established by an appropriate calibration of the apparatus. It should be noted parenthetically that this can be simply and accurately done by the known DSC apparatus shown in FIG. 6. In the present invention, the structure of the Q-DSC apparatus developed makes it also possible to transfer a predetermined amount of electric power or heat to the sample. Returning now to the apparatus of the present invention, in FIG. 7c temperatures corresponding to breaking points a, c, d and e in curve $\int$Q-DTA$_T$ mark accurately the limits of elementary processes, thus the magnitude of partial enthalpy variations $\Delta J_1$, $\Delta J_2$, $\Delta J_3$ and $\Delta J_4$ can be determined conveniently. Their proportionality is ensured by the measuring technique so that the rate of enthalpy variation is kept constant, as is shown in curve Q-DTA$_t$ in FIG. 4c. The accuracy of the determination is higher here than in other known procedures, since in the latter ones, the course of curves is deteriorated by the experimental conditions not only from the point of view of temperature, but also from that of heat content. The quasi-isothermal measuring technique eliminates this deterioration as well.

The procedure and apparatus realising it described in this invention may also be very useful in combination with other thermal analytical investigations. We should distinguish two modes of operation: In one of them, we study the sample by a derivatograph suitable for the measurement of more variables simultaneously so that the heating programme is controlled by a quasi-isothermal heating unit, and curve Q-DTA$_t$ thus obtained is transformed to signal $\int$Q/IDTA$_T$ or eventually to d$\int$DTA$_T$ which are then recorded together with the other variables, such as the thermogravimetric, Q-TG$_T$, thermal gas titrimetric, Q-TGT$_T$, thermal dilatometric, Q-TD$_T$, etc. curves as functions of sample temperature. In the other mode of operation, we control the heating of the furnace by the signals of the rate of weight change Q-DTG, or the rate of consumption of titrating solution in thermal gas titrimetry Q-DTGT, or the dilatation rate of the pressed specimen Q-DTD etc., and we obtain the Q-TG, Q-TGT, Q-TD, etc. signals this way. Independently of this measuring and heating control system, but simultaneously with the above curves, we measure the enthalpy change rate of the sample, Q-DTA$_t$, and the temperature change of the sample as well. These latter signals are transformed according to the present invention, and the signals $\int$Q-DTA$_T$ and d$\int$Q-DTA$_T$ thus obtained are recorded together with the other curves as functions of sample temperatures. Experiments carried out by the two different techniques do not lead necessarily to the same result, but from their difference very valuable conclusions can be drawn.

It follows from the above that the process and apparatus according to the invention described is only one example for each from among many possibilities. However, it is common in all the solutions that every one follows the procedure described in this invention, every one realises the same purpose and every one provides the same result At present, the majority of apparatuses operate with computers, and instead of electronic elements, the data of measured signals are collected, stored, processed and displayed in the computer controlled by an appropriate software. Thus the process of the invention can also be realised in another embodiment by a computer.

Various modifications in structure and/for function may be made to the disclosed embodiments by one skilled in the art without departing from the scope of the invention as defined by the claims.

What is claimed is:

1. Thermal analysis process for investigation of thermal phase transformations, wherein a sample (2) and a reference substance (1) are placed into a furnace (3) with rising temperature of a predetermined rate operated by a programmed temperature controller (4), the temperatures of sample (2) and reference substance (1) are sensed by temperature sensors (5, 6); the difference between the temperatures ($T_s'$, $T_r'$) of the sample (2) and reference substance (1) is determined by a temperature difference measuring device (9) having an output signal ($Q\text{-}DTA_t$) which is proportional to the temperature difference between the temperature ($T_s'$) of the sample (2) and the temperature ($T_r'$) of the reference substance (1) said signal ($Q\text{-}DTA_t$) is generated by the known quasi-static heating technique, wherein said temperature difference is automatically controlled continuously so that said thermal phase transformation of the sample takes place at a constant rate, characterised in that said output signal ($Q\text{-}DTA_t$) which is a function of time t, is integrated with respect to time by an integrating unit (18); and in that said output signal ($\int Q\text{-}DTA_t$) of said integrating unit (18) is further transformed into a signal ($\int Q\text{-}DTA_T$) dependent on the temperature $T_s'$ of the sample.

2. The process in claim 1 characterised by a further differentiation of integrated signal ($\int Q\text{-}DTA_T$) in order to obtain signal ($d\int Q\text{-}DTA_T$).

3. A thermal analysis system for investigation of thermal phase transformations using a DTA device know per se, wherein a sample (2) and a reference substance (1) are placed into a furnace (3) with rising temperature of a predetermined rate; said furnace (3) is connected to a programmed temperature controller (4); both the sample (2) and reference substance (1) are coupled to temperature sensors (5, 6) coupled oppositely; a temperature measuring device (7) measuring the sample temperature, $T_s$ which is coupled to the free contacts of the sensors (5, 6) in series; a symmetrising resistor (8) coupled to the free contacts of said oppositely coupled temperature sensors (5, 6); a differentiating unit (10) connected in series to a temperature difference measuring device (9) sensing the difference between sample (2) and reference substance (1), the output of said device (9) is connected to a display means and a recorder, and the output of said differentiating unit (10) is also connected to a device signal sensor (11) and the recorder, a deflection of the device signal sensor (11) representing a change of value measured by the device signal sensor is sensed by limit switches (12) the output contacts of which are connected to the input of the programmed temperature controller (4) via a multifunction switching unit (14), and, similarly, the output contact of the temperature difference measuring unit (9) is also coupled to switching unit (14) characterised by an integrating unit (18) connected to the output of said temperature difference measuring unit (9) the output of which integrating unit (18) is a time dependent output signal connected to a signal converter (19), having further two inputs coupled to said temperature measuring device (7) measuring the sample temperature; said signal converter (19) generating a temperature dependent transformed signal $\Delta t/\Delta(T_s)$ which is connected to a display (20) coupled to a recorder.

4. Thermal analysis system for investigation of thermal phase transformations using a DSC-device known per se, wherein a sample (230) and a reference substance (240) are placed in furnace (300) having a double heating system, one heating element (290) of which is controlled by a programmed temperature controller (4), the inputs of said controller (4) are connected to a temperature difference measuring unit (9), the inputs of said measuring unit (9) are connected to temperature sensors (5, 6) measuring the temperature of the sample and the reference substance, respectively; a first output of said measuring unit (9) is connected to a limit switch (310) coupled to second heating elements (280, 270) and to a differentiating unit (130), the second output of said measuring unit (9) is connected to a recorder, characterised by an integrating unit (18) for integrating the output of said temperature difference measuring sensor (9) the time dependent output signal of which integrating unit (18) is connected to a signal converter (19) for transforming said time dependent signal to a temperature dependent transformed signal which is connected to a display (20) coupled to a recorder.

5. The apparatus according to claim 3, characterised by the connection of a differentiating unit (21) to the output of said signal converter (19), the output of which is also connected to said display and recorder.

* * * * *